United States Patent
Minagawa et al.

(10) Patent No.: US 11,660,596 B2
(45) Date of Patent: May 30, 2023

(54) MEDICAL ANALYSIS DEVICE AND CELL ANALYSIS METHOD

(71) Applicants: SUMITOMO RUBBER INDUSTRIES, LTD., Kobe (JP); YAMAGATA UNIVERSITY, Yamagata (JP)

(72) Inventors: Yasuhisa Minagawa, Kobe (JP); Masaru Tanaka, Yonezawa (JP); Haruka Emura, Yonezawa (JP); Kazuki Suto, Yonezawa (JP)

(73) Assignees: SUMITOMO RUBBER INDUSTRIES, LTD., Kobe (JP); YAMAGATA UNIVERSITY, Yamagata (JP)

(*) Notice: Subject to any disclaimer, the term of this patent is extended or adjusted under 35 U.S.C. 154(b) by 157 days.

(21) Appl. No.: 16/830,016

(22) Filed: Mar. 25, 2020

(65) Prior Publication Data
US 2020/0338554 A1  Oct. 29, 2020

(30) Foreign Application Priority Data
Apr. 23, 2019 (JP) .............................. JP2019-082075

(51) Int. Cl.
*B01L 3/00* (2006.01)
(52) U.S. Cl.
CPC ............... *B01L 3/502715* (2013.01); *B01L 3/502776* (2013.01); *B01L 2300/0829* (2013.01); *B01L 2300/161* (2013.01)
(58) Field of Classification Search
None
See application file for complete search history.

(56) References Cited

U.S. PATENT DOCUMENTS

| | | | |
|---|---|---|---|
| 2003/0148401 A1* | 8/2003 | Agrawal | B01L 3/5085 435/7.9 |
| 2005/0003421 A1* | 1/2005 | Besemer | C07H 21/00 435/7.1 |
| 2009/0186777 A1* | 7/2009 | Lee | B01L 3/5085 506/15 |
| 2014/0272925 A1 | 9/2014 | Menon et al. | |
| 2018/0087017 A1 | 3/2018 | Minagawa et al. | |

FOREIGN PATENT DOCUMENTS

| | | | |
|---|---|---|---|
| JP | 2005-523981 A | 8/2005 | |
| JP | 2011-83244 A | 4/2011 | |
| JP | 2018-59901 A | 4/2018 | |
| WO | WO 03/091392 A2 | 11/2003 | |
| WO | WO 03/093357 A1 | 11/2003 | |
| WO | WO-03091392 A2 * | 11/2003 | B01J 19/0046 |
| WO | WO 2017/087032 A1 | 5/2017 | |

OTHER PUBLICATIONS

Yap, Fung Ling; Zhang, Yong, "Protein Micropatterning Using Surfaces Modified by Self-Assembled Polystyrene Microspheres" Langmuir. 2005, 21(12), 5233-5236. (Year: 2005).*

* cited by examiner

*Primary Examiner* — Matthew D Krcha
(74) *Attorney, Agent, or Firm* — Birch, Stewart, Kolasch & Birch, LLP

(57) ABSTRACT

The present invention provides a medical analysis device and a cell analysis method, which can capture specific cells such as many types of cancer cells including cancer cells not expressing EpCAM and stem cells. Provided is a medical analysis device including a well portion, the well portion having a hydrophilic silane compound layer formed at least partly on the inner surface thereof.

9 Claims, 2 Drawing Sheets

A-A cross-sectional view

FIG. 1-1(a-1)

A-A cross-sectional view

MEDICAL ANALYSIS DEVICE AND CELL ANALYSIS METHOD

The present invention relates to a medical analysis device and a cell analysis method, which can capture specific cells present in blood or biological fluid, such as cancer cells and stem cells present in blood or biological fluid.

BACKGROUND ART

Cancer cells, when formed, are known to appear in due course in blood or biological fluid. Such cancer cells in blood are called "circulating tumor cells (CTCs)". Thus, it has been expected that the circulating tumor cells may be analyzed, e.g., to evaluate the cancer-treating effect, predict prognosis life expectancy, predict the effects of anticancer drugs before administration, or examine treatment methods based on genetic analysis of cancer cells (see, Patent Literature 1).

Unfortunately, however, since the number of circulating tumor cells is very small (several to hundreds of cells/1 mL of blood), such cancer cells are difficult to capture.

For example, the CellSearch System is known as a technique for capturing circulating tumor cells. This technique, which involves an antigen-antibody reaction (capture by EpCAM antibody), can only capture cancer cells expressing EpCAM, and the types of cancer cells that can be captured are limited.

CITATION LIST

Patent Literature

Patent Literature 1: JP 2005-523981 T

SUMMARY OF INVENTION

Technical Problem

The present invention aims to solve the above problems and provide a medical analysis device and a cell analysis method, which can capture specific cells such as many types of cancer cells including cancer cells not expressing EpCAM and stem cells.

Solution To Problem

The present invention relates to a medical analysis device, including a well portion, the well portion having a hydrophilic silane compound layer formed at least partly on an inner surface thereof.

The hydrophilic silane compound is preferably a compound represented by the following formula (I):

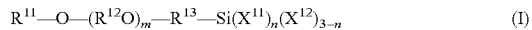

(I)

wherein $R^{11}$ represents a monovalent hydrocarbon group; $R^{12}$ and $R^{13}$ are the same or different and each represent a divalent hydrocarbon group; each $X^{11}$ independently represents an alkoxy group; each $X^{12}$ independently represents a monovalent hydrocarbon group or a halogen group; m represents 1 to 50; and n represents 0 to 3.

The silane compound of formula (I) is preferably a compound represented by the following formula (I-1):

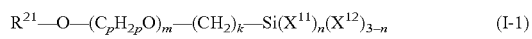

(I-1)

wherein $R^{21}$ represents a methyl group or an ethyl group; each $X^{11}$ independently represents an alkoxy group; each $X^{12}$ independently represents a monovalent hydrocarbon group or a halogen group; p represents 1 to 8; m represents 1 to 50; n represents 0 to 3; and k represents 1 to 20.

The hydrophilic silane compound layer in the medical analysis device preferably has fibronectin adsorbed thereto.

Another aspect of the present invention relates to a cell analysis method for examining cells present in blood or biological fluid using the medical analysis device.

The cell analysis method preferably includes: fractionating blood or biological fluid by centrifugation to collect specific cells from the blood or biological fluid; capturing the specific cells from the collected liquid onto the hydrophilic silane compound layer using the medical analysis device; and examining the specific cells.

In the cell analysis method, a separation liquid is preferably used in the fractionation by centrifugation.

The separation liquid preferably has a density of 1.060 to 1.115 g/mL.

The centrifugation is preferably carried out using a container whose inner surface at least partly has a contact angle with water of 30 degrees or less.

Advantageous Effects of Invention

The medical analysis device of the present invention includes a well portion having a hydrophilic silane compound layer formed at least partly on the inner surface thereof. Such a medical analysis device can capture specific cells such as many types of cancer cells including cancer cells not expressing EpCAM and stem cells. Thus, for example, it is possible to sufficiently capture specific cells such as cancer cells and stem cells from blood or biological fluid while reducing adsorption or adhesion of other proteins and cells, thereby selectively capturing the specific cells such as cancer cells and stem cells.

DESCRIPTION OF EMBODIMENTS

[Medical Analysis Device]

The present invention relates to a medical analysis device including a well portion which has a hydrophilic silane compound layer formed at least partly on the inner surface thereof. The hydrophilic silane compound layer in the medical analysis device preferably has fibronectin adsorbed thereto.

Since the hydrophilic silane compound layer is formed at least partly on the inner surface of the well portion, the hydrophilic silane compound can exhibit a very significantly improved ability to adhere (adsorb) to specific cells such as cancer cells and stem cells. Thus, greatly improved capture of specific cells such as cancer cells and stem cells can be provided while reducing capture of other cells such as platelets. As a result, an effect which could never be produced when proteins are present at high levels can be achieved in selectively capturing the specific cells.

Specifically, since the number of tumor cells (e.g., cancer cells) appearing in biological fluid, such as circulating tumor cells (several to hundreds of cells/1 mL of blood), is very small, it is important to capture as many tumor cells as possible from the sampled biological fluid to analyze them. In the present invention, the hydrophilic silane compound layer formed may be brought into contact with biological fluid such as blood to adsorb or adhere a lot of tumor cells and the like from the biological fluid onto the hydrophilic silane compound layer. Then, it is expected that by counting the number of adsorbed specific sells such as tumor cells, one can determine the number of specific cells in the blood or biological fluid, e.g., in order to evaluate the cancer-treating effect. Moreover, the captured specific cells may be cultured and then used to determine the effects of drugs such as anticancer drugs. This allows one to determine the effects of drugs such as anticancer drugs ex vivo before administration, and also helps to screen drugs such as anticancer drugs.

Examples of preferred embodiments of the present invention are described below with reference to drawings.

Figure 1:
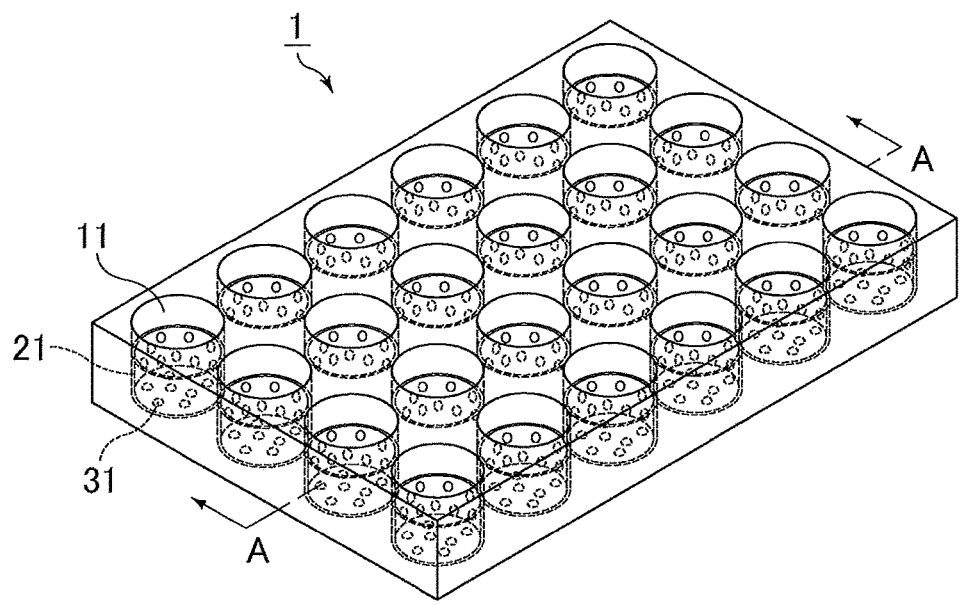
FIGS. 1-1(*a*) and (*a*-1) and FIGS. 1-2(*b*) and (*c*) illustrate exemplary schematic views of a multi-well plate, chamber slides, and a single well, each of which includes a well portion in which a hydrophilic silane compound layer having fibronectin adsorbed thereto is formed on the inner surface.
Figure 1A:
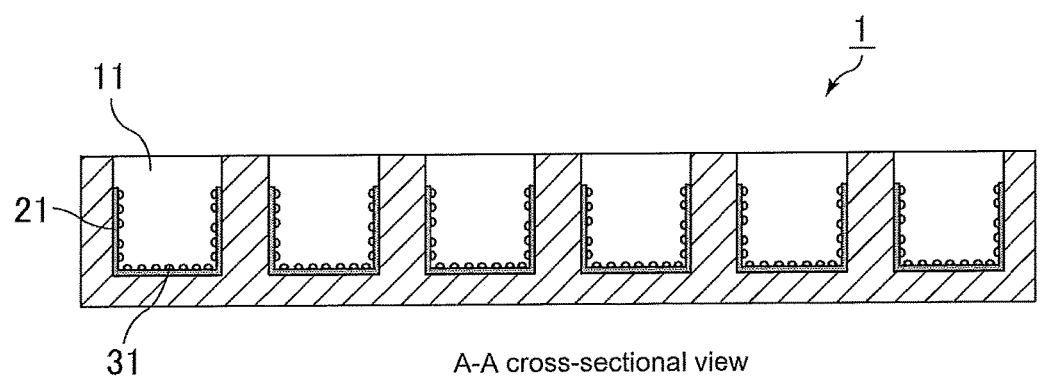
Figures 1, 2:
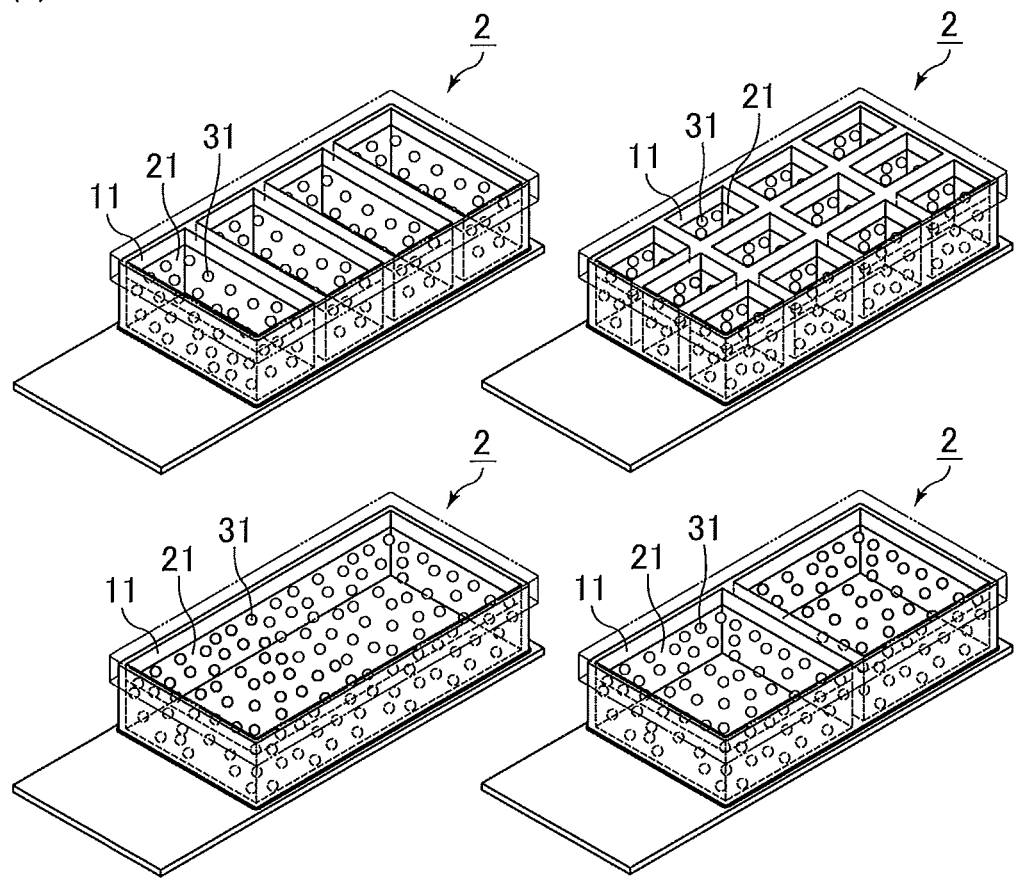
Figures 1, 2:
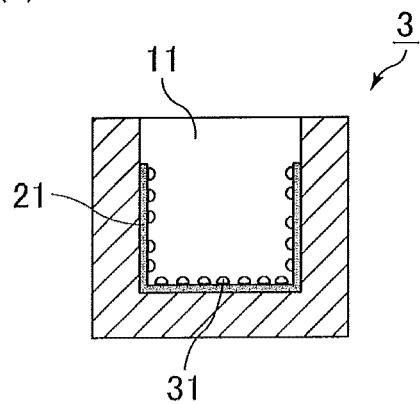

Exemplary medical analysis devices include devices using a multi-well plate (FIG. 1-1(a), a chamber slide (FIG. 1-2(b)), or a single well (dish, FIG. 1-2(c)). These devices may be used to capture specific cells such as cancer cells and stem cells.

The medical analysis device using a multi-well plate includes a multi-well plate 1 in which wells 11 are arranged in a matrix form as shown in FIG. 1-1(a), for example. The multi-well plate 1 has a plurality of wells 11 having a circular opening. The medical analysis device using a chamber slide includes a chamber slide 2 as shown in FIG. 1-2(b), for example. The chamber slide 2 is configured to include, on a substrate of a material such as glass, a chamber into which a sample (e.g., blood, biological fluid) may be injected, and has a rectangular well(s) 11.

Each well 11 is a recess into which, for example, blood or biological fluid may be injected, and can be used to confirm the presence or absence of specific cells in the injected blood or biological fluid, count the number of specific cells, culture the specific cells, determine the effects of drugs, and/or screen the drugs.

Although FIG. 1-1(a) shows an exemplary 24-well plate having 24 wells 11 arranged in 4 rows by 6 columns, it is sufficient for the multi-well plate 1 to have at least two wells 11, and any number of wells 11 may be provided. Examples other than the 24-well plate include general multi-well plates in which the number of wells 11 is 6, 96, 384, etc. FIG. 1-2(b) shows an exemplary chamber slide with one well (single well) and exemplary chamber slides with two, four, or 12 separate wells.

The structural material of the multi-well plate 1, chamber slide 2, or single well 3 (dish) in the medical analysis device should be highly transparent enough for observation during the cell analysis, and examples include acrylic resins (polyacrylic resins) such as polymethyl acrylate, polymethyl methacrylate, polyacrylic acid, and polymethacrylic acid, cycloolefin resins (polycycloolefins), carbonate resins (polycarbonates), styrene resins (polystyrenes), polyester resins such as polyethylene terephthalate (PET), polydimethylsiloxanes, and glass (e.g., borosilicate glass, soda-lime glass). The structural material should be highly hydrophilic for coating with a hydrophilic silane compound, and preferred are polyacrylic resins and soda-lime glass.

The structural material of the medical analysis device for capturing cells may include a metal material. Examples of the metal material include metals such as stainless steel, nickel-titanium alloys, iron, titanium, aluminum, tin, and zinc-tungsten alloys. From the standpoint of biocompatibility, stainless steel and nickel-titanium alloys are preferred among these.

In the medical analysis device, a hydrophilic silane compound layer 21 is formed on the inner surface of each well 11 (well portion), but a primer layer (not shown) may be formed between the structural material and the hydrophilic silane compound layer 21. The primer layer may suitably be a layer formed from an alkoxy group-containing silane compound other than the hydrophilic silane compound, which will be described later. The number of carbon atoms of the alkoxy group is preferably 1 to 22, more preferably 1 to 16. The alkoxy group is preferably at least one selected from the group consisting of a methoxy group, an ethoxy group, a propoxy group, and a butoxy group. The alkoxy group-containing silane compound more preferably contains an ethoxy group and/or a butoxy group, still more preferably an ethoxy group and a butoxy group, among others.

The alkoxy group-containing silane compound may contain a hydrocarbon group such as an alkyl group. The number of carbon atoms of the alkyl group is preferably 1 to 6, more preferably 1 to 4. Examples of the alkyl group include C1-C8 alkyl groups such as a methyl group, an ethyl group, a n-propyl group, an isopropyl group, a n-butyl group, an isobutyl group, a sec-butyl group, and a tert-butyl group.

Examples of the silane compound include monoalkoxysilanes having one alkoxy group, dialkoxysilanes having two alkoxy groups, trialkoxysilanes having three alkoxy groups, and tetraalkoxysilanes having four alkoxy groups. The silane compound may be, for example, a compound represented by the following formula (1):

$$R^{11}{}_k Si(OR^{12})_{4-k} \qquad (1)$$

wherein each $R^{11}$ or each $R^{12}$ independently represents a C1-C8 saturated or unsaturated hydrocarbon group, and $R^{11}$ and $R^{12}$ may be the same as or different from each other; and k represents an integer of 0 to 3.

Among these compounds, compounds having two or more alkoxy groups are preferred, with compounds having three or more alkoxy groups being more preferred.

$R^{11}$ and $R^{12}$ in formula (1) each preferably have 1 to 6 carbon atoms, more preferably 1 to 4 carbon atoms. $R^{11}$ and $R^{12}$ are each preferably a saturated hydrocarbon group.

Specific examples of the monoalkoxysilanes include trimethylmethoxysilane, trimethylethoxysilane, trimethylpropoxysilane, triethylmethoxysilane, triethylethoxysilane, and tripropylpropoxysilane. Specific examples of the dialkoxysilanes include dimethyldimethoxysilane, dimethyldiethoxysilane, dimethyldipropoxysilane, diethyldimethoxysilane, diethyldiethoxysilane, methylethyldimethoxysilane, methylethyldiethoxysilane, and dipropyldimethoxysilane. Specific examples of the trialkoxysilanes include methyltrimethoxysilane, methyltriethoxysilane, methyltripropoxysilane, ethyltrimethoxysilane, ethyltriethoxysilane, propyltrimethoxysilane, propyltriethoxysilane, and butyltrimethoxysilane. Specific examples of the tetraalkoxysilanes include tetramethoxysilane, tetraethoxysilane, tetrapropoxysilane, tetrabutoxysilane, dibutoxydiethoxysilane, butoxytriethoxysilane, and ethoxytriethoxysilane.

The silane compound may also suitably be a compound represented by the following formula (2):

$$(R^{21}O)_m Si(OR^{22})_n \qquad (2)$$

wherein $R^{21}$ and $R^{22}$ are the same or different and each represent a C1-C8 saturated or unsaturated hydrocarbon group; and m+n=4 with on average.

$R^{21}$ and $R^{22}$ in formula (2) each preferably have 1 to 6 carbon atoms, more preferably 1 to 4 carbon atoms. $R^{21}$ and $R^{22}$ are each preferably a saturated hydrocarbon group.

Examples of the silane compound of formula (2) include a butoxy/ethoxy tetraalkoxysilane ("Primer coat PC-3B" available from Fluoro Technology) represented by the following formula (2-1):

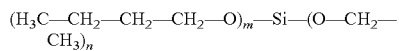

wherein m+n=4 with m>n>0 on average.

Each well 11 is a blind hole which is provided in, for example, the multi-well plate 1, chamber slide 2, or single well 3 and has an opening through which blood or biological fluid may be injected into the well 11. If the presence of specific cells such as cancer cells and stem cells is confirmed, a culture fluid for culturing the specific cells may also be injected.

The size of the opening of each well 11 is not limited and may correspond to the diameter R and depth D of a conventional multi-well plate 1 or single well 3 (dish) or the length X, width Y, and depth D of a conventional chamber slide 2. Although in FIG. 1-1(a) and FIG. 1-2(b), the inner side surface of each well 11 is substantially vertical to the opposite faces of the plate of the multi-well plate 1 or of the slide of the chamber slide 2, the inner side surface of each well 11 may be inclined to taper from the opening to the bottom. Alternatively, the inner side surface may be inclined to flare out from the opening to the bottom.

Although the wells 11 in FIG. 1-1(a) and FIG. 1-2(b) have a circular or rectangular opening, the openings of the wells 11 may be of any shape (e.g., triangle, oval) that allows a sample to be introduced therethrough.

The multi-well plate 1 or chamber slide 2 may be one in which the plurality of wells 11 are separable. In the case where a plurality of wells are provided, they may be separated into wells for counting the number of specific cells and for culturing the specific cells. For example, the presence or absence of cancer cells may first be confirmed in the counting wells, and if the presence is confirmed, the cancer cells may be cultured in the culturing wells and then used to determine the effects of drugs.

In the multi-well plate 1, chamber slide 2, single well 3 (dish), or the like of the medical analysis device, a hydrophilic silane compound layer is formed at least partly on the inner surface of each well 11. From the standpoint of the above-mentioned advantageous effect, the hydrophilic silane compound layer in the medical analysis device preferably has fibronectin adsorbed thereto. FIG. 1-1(a) and FIG. 1-1(a-1) illustrate an exemplary multi-well plate 1 in which a hydrophilic silane compound layer 21 is formed and, further, fibronectin 31 is adsorbed onto the hydrophilic silane compound layer 21. Similarly, the chamber slide 2 or single well 3 (dish) may be one in which a hydrophilic silane compound layer is formed and fibronectin is adsorbed onto the layer.

Once blood or biological fluid is introduced into the well 11, specific cells such as cancer cells and stem cells present in the blood or biological fluid will be adsorbed onto the hydrophilic silane compound layer 21, optionally with fibronectin 31 adsorbed thereto, while reducing adsorption of other cells such as platelets and erythrocytes. Thus, the specific cells can be adsorbed onto the hydrophilic silane compound layer 21 by introducing and retaining blood or biological fluid in the well for a predetermined time, followed by washing. Then, it is expected that by counting the number of adsorbed specific cells, one can determine the number of cancer cells in the blood or biological fluid, e.g., in order to evaluate the cancer-treating effect.

A hydrophilic silane compound layer 21 formed from a hydrophilic silane compound is provided at least partly on the inner surface of each well 11.

From standpoints such as selective adsorption or adhesion of specific cells, the hydrophilic silane compound is preferably, for example, a polyalkylene oxide group-containing hydrophilic silane compound. Suitable examples include [alkoxy(polyalkyleneoxy)alkyl]trialkoxysilanes such as [methoxy(polyethyleneoxy)propyl]trimethoxysilane.

For example, the polyalkylene oxide group-containing hydrophilic silane compound may suitably be a compound represented by the following formula (I):

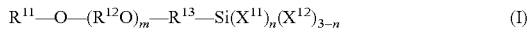

wherein $R^{11}$ represents a monovalent hydrocarbon group; $R^{12}$ and $R^{13}$ are the same or different and each represent a divalent hydrocarbon group; each $X^{11}$ independently represents an alkoxy group; each $X^{12}$ independently represents a monovalent hydrocarbon group or a halogen group; m represents 1 to 50; and n represents 0 to 3.

In formula (I), the monovalent hydrocarbon group as $R^{11}$ may be, for example, a linear, cyclic, or branched alkyl, alkenyl, aryl, or aralkyl, particularly preferably alkyl group. The monovalent hydrocarbon group may be substituted or unsubstituted. The number of carbon atoms of $R^{11}$ in formula (I) is preferably 1 to 18, more preferably 1 to 10, still more preferably 1 to 4. Specific examples of the monovalent hydrocarbon group as $R^{11}$ include substituted or unsubstituted methyl, ethyl, n-propyl, isopropyl, n-butyl, isobutyl, sec-butyl, and tert-butyl groups.

The divalent hydrocarbon group as $R^{12}$ or $R^{13}$ in formula (I) may be a linear, cyclic, or branched group, particularly preferably a linear group. The divalent hydrocarbon group may be substituted or unsubstituted.

Specific examples of the divalent hydrocarbon group as $R^{12}$ in formula (I) include substituted or unsubstituted C1-C30 alkylene, C2-C30 alkenylene, C5-C30 cycloalkylene, C6-C30 cycloalkylalkylene, C6-C30 arylene, and C7-C30 aralkylene groups. Among these, $R^{11}$ is preferably a substituted or unsubstituted C1-C18 alkylene, more preferably C1-C10 alkylene, still more preferably C1-C6 alkylene group. $R^{13}$ is preferably a substituted or unsubstituted C1-C20 alkylene, more preferably C1-C14 alkylene, still more preferably C1-C12 alkylene group. Specific examples of $R^{11}$ or $R^{13}$ include substituted or unsubstituted methylene, ethylene, trimethylene, tetramethylene, pentamethylene, and hexamethylene groups.

In formula (I), the alkoxy group as $X^{11}$ may be a branched or unbranched group. The carbon number of the alkoxy group in formula (I) is preferably 1 to 12, more preferably 1 to 8, still more preferably 1 to 5. Specific examples of the alkoxy group include methoxy, ethoxy, n-propoxy, isopropoxy, n-butoxy, iso-butoxy, sec-butoxy, tert-butoxy, pentyloxy, hexyloxy, heptyloxy, 2-ethylhexyloxy, octyloxy, and nonyloxyl groups.

Examples of the monovalent hydrocarbon group as $X^{12}$ in formula (I) include those mentioned for the monovalent hydrocarbon group as $R^{11}$. Examples of the halogen group (halogen atom) as $R^{12}$ include fluorine, chlorine, and bromine.

In formula (I), m is preferably 1 to 40, more preferably 1 to 30, still more preferably 1 to 25.

In formula (I), n is preferably 1 to 3, more preferably 2 to 3.

In formula (I), $R^{11}$, $R^{12}$, $R^{13}$, $X^{11}$, and $X^{12}$ each may be substituted with any substituent, such as a hydroxyl group and other functional groups.

For example, the hydrophilic silane compound of formula (I) may suitably be a hydrophilic silane compound represented by the following formula (I-1):

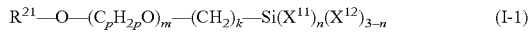
$$R^{21}-O-(C_pH_{2p}O)_m-(CH_2)_k-Si(X^{11})_n(X^{12})_{3-n} \quad (I\text{-}1)$$

wherein $R^{21}$ represents a methyl group or an ethyl group; each $X^{11}$ independently represents an alkoxy group; each $X^{12}$ independently represents a monovalent hydrocarbon group or a halogen group; p represents 1 to 8; m represents 1 to 50; n represents 0 to 3; and k represents 1 to 20.

In formula (I-1), $X^{11}$, $X^{12}$, m, and n are as defined above; p is preferably 1 to 5, more preferably 1 to 3; the —$C_pH_{2p}O$— group may be linear or branched, particularly preferably linear; and k is preferably 1 to 16, more preferably 1 to 12.

The thickness of the hydrophilic silane compound layer 21 (the layer formed from the hydrophilic silane compound) is preferably 1 to 30 nm, more preferably 2 to 20 nm. When the thickness is adjusted within the range indicated above, selective adsorption or adhesion of specific cells such cancer cells and stem cells and low adsorption of other proteins and cells can be well achieved.

From the standpoint of adsorption of fibronectin 31 onto the hydrophilic silane compound layer 21, it is suitable to use a solution, dispersion, or other mixture preferably having a fibronectin concentration adjusted to 0.5 to 500 μg/mL, more preferably 1 to 250 μg/mL. When the concentration is adjusted within the range indicated above, selective adsorption or adhesion of specific cells such cancer cells and stem cells and low adsorption of other proteins and cells can be well achieved.

The medical analysis device of the present invention can be produced, for example, by preparing a multi-well plate 1, chamber slide 2, single well 3 (dish), or the like including a well(s) 11 in which a hydrophilic silane compound layer 21, optionally with fibronectin 31 adsorbed thereto, is formed on the inner surface as shown in FIGS. 1, optionally followed by addition of other components (parts).

Specifically, in the preparation of a multi-well plate 1, chamber slide 2, single well 3 (dish), or the like on which a hydrophilic silane compound layer 21 is formed, a hydrophilic silane compound may be dissolved or dispersed in any solvent to prepare a hydrophilic silane compound solution or dispersion, and then the inner surface of each well 11 may be entirely or partly coated with the hydrophilic silane compound solution or dispersion by a known method, such as (1) by injecting the hydrophilic silane compound solution or dispersion into each well 11 and retaining it for a predetermined time, or (2) by applying (spraying) the hydrophilic silane compound solution or dispersion to the inner surface of each well 11 and retaining it for a predetermined time. Thus, a multi-well plate 1, chamber slide 2, single well 3 (dish), or the like provided with a layer formed from the hydrophilic silane compound can be produced.

The solvent, injection method, application (spraying) method, and other conditions may be conventionally known materials or methods.

The retention time in the method (1) or (2) may be selected appropriately according to the size of the well 11, the type of liquid introduced, and other factors. The retention time is preferably five minutes to 10 hours, more preferably 10 minutes to five hours, still more preferably 15 minutes to two hours. After the retention, the excess hydrophilic silane compound solution or dispersion may be discharged, followed by drying, as needed.

Next, fibronectin 31 may be adsorbed onto the formed hydrophilic silane compound layer 21 by any known method, for example, by bringing the hydrophilic silane compound layer 21 into contact with a buffer solution (e.g., phosphate buffered saline (PBS)) containing fibronectin 31 by a known method, and leaving them at a predetermined temperature for a predetermined time, optionally followed by washing. The temperature and time may be selected as appropriate, and may be, for example, about 10 to 60° C. and about 0.1 to 10 hours, respectively.

Then, other components may be added as needed to the prepared multi-well plate 1, chamber slide 2, single well 3 (dish), or the like in which a hydrophilic silane compound layer 21 with fibronectin 31 adsorbed thereto is formed partly on the inner surface of each well 11, to produce a medical analysis device.

In the present invention, components with fibrinogen adsorbed thereto may preferably be used as such other components. When the blood or biological fluid to be analyzed is brought into contact with a component with adsorbed fibrinogen, which is involved in the adhesion of blood cells, the number of blood cells can be reduced prior to the analysis, thereby resulting in improved adhesion or adsorption of specific cells such as cancer cells and stem cells.

[Cell Analysis Method]

The cell analysis method of the present invention includes examining cells present in blood or biological fluid using the medical analysis device described above. As mentioned earlier, the medical analysis device of the present invention provides improved capture of specific cells such as cancer cells and stem cells while reducing capture of other cells such as platelets, thereby achieving an effect of selectively capturing the specific cells. It is therefore expected that such a device may be used to examine cells present in blood or biological fluid, e.g., in order to evaluate the cancer-treating effect, determine the effects of drugs such as anticancer drugs ex vivo, and/or screen drugs such as anticancer drugs, as described above.

From the standpoint of enrichment of specific cells for improved capture, the cell analysis method preferably includes: first fractionating blood or biological fluid by centrifugation to collect specific cells from the blood or biological fluid; capturing the specific cells from the collected liquid onto the hydrophilic silane compound layer using the medical analysis device; and examining (analyzing) the specific cells.

From the standpoint of collection of specific cells, the inner surface of the container used in the centrifugation preferably at least partly has a contact angle with water of 30 degrees or less, more preferably 20 degrees or less, still more preferably 10 degrees or less.

The contact angle with water may be measured by dropping 2 μL of distilled water onto the inner surface of the container and 30 seconds later measuring the contact angle by the θ/2 method (at room temperature).

The centrifugation may be carried out by known methods, for example, by using a known centrifugal separator.

The centrifugation is preferably carried out at a centrifugal force of 200 to 3,000 G (×G). A centrifugal force of 200 G or higher leads to improved separation of blood cells and reduction in the loss of specific cells (the loss due to the specific cells being incorporated into the fraction of red blood cells and the like), thereby being effective in selectively capturing specific cells. A centrifugal force of 3000 G or lower provides reduced stress on specific cells, thereby maintaining their original nature. The centrifugal force is more preferably 300 to 2,800 G, still more preferably 400 to 2,500 G.

The duration and temperature of the centrifugation may be appropriately selected from standpoints such as separation of blood cells. For example, the centrifugation may be performed for 1 to 120 minutes, preferably 1 to 60 minutes, at 2° C. to 40° C., preferably 3° C. to 30° C.

In the centrifugation, preferably a separation liquid is used in the fractionation by centrifugation. This enables suitable fractionation into a mononuclear cell layer containing specific cells (e.g., cancer cells), a layer containing red blood cells and the like, and other layers.

The separation liquid to be used in density-gradient centrifugation may be prepared such that it has a specific gravity suited for fractionating cells in blood and also has an osmotic pressure and pH that do not destroy cells. The medium used may be one that is usable in density-gradient centrifugation. The separation liquid preferably has a specific gravity at 20° C. of 1.060 to 1.115 g/mL. The separation liquid preferably has a pH of 4.5 to 7.5.

Typical examples of the medium (separation liquid) include sucrose, ficoll (a copolymer of sucrose and epichlorohydrin), and percoll (polyvinylpyrrolidone-coated colloidal silica product). Examples of commercial products of ficoll include Ficoll-Paque PLUS (Pharmacia Biotech), Histopaque-1077 (Sigma-Aldrich Japan), and Lymphoprep (Nycomed, Oslo, Norway). Examples of commercial products of percoll include Percoll (Sigma-Aldrich Japan).

From the standpoint of collection of specific cells, the separation liquid preferably has a density (20° C.) of 1.060 to 1.115 g/mL, more preferably 1.060 to 1.085 g/mL.

Through the fractionation by centrifugation and collection as described above, specific cells can be collected without loss. It is thus possible to prepare samples from which red blood cells and platelets have been separated and removed and which contain a higher concentration of specific cells such as cancer cells and stem cells.

In order to further reduce red blood cells in the fraction to be collected, preferably a hemolytic agent is mixed with (added to) the blood or biological fluid, followed by the centrifugation. Hemolytic agents physically or chemically act on red blood cells to lyse the red blood cells. The hemolytic agent used may be a conventional one. Examples include ammonium chloride, synthetic surfactants, and alcohols.

The centrifugation is preferably performed after blood cells in the blood or biological fluid are agglutinated. In other words, the centrifugation is preferably preceded by agglutinating blood cells in the blood or biological fluid. Blood cells may be agglutinated by any method that can cause such agglutination. Among such methods, those based on antigen-antibody reactions are suitable. Specifically, methods based on agglutination reactions such as hemagglutination may be suitably used.

When the blood cells in the blood or biological fluid are agglutinated via hemagglutination to prepare a sample containing agglutinates in the agglutination step, the agglutinates including blood cells can be removed by the subsequent centrifugation of the sample. Thus, the specific cells (e.g., cancer cells and stem cells) remaining at a high concentration in the sample can be effectively captured onto the hydrophilic silane compound layer.

The agglutination of blood cells may be suitably carried out using, for example, an antibody reagent for agglutinating red and white blood cells (an antibody composition for agglutinating red and white blood cells). In spite of the fact that some white blood cells having specific gravities close to the specific cells such as cancer cells can be poorly separated by centrifugation, when red and white blood cells are bound and agglutinated via an antigen-antibody reaction using the antibody composition, the specific cells can be well separated not only from red blood cells, platelets, and the like having specific gravities different from the specific cells, but also from white blood cells. Thus, it is possible to improve adhesion and capture of the specific cells.

The blood or biological fluid may be diluted before the agglutination of blood cells, followed by the centrifugation. The dilution may be performed using a buffer solution such as a phosphate buffered saline (PBS) having the same pH as human blood (about 7.4) or a liquid medium such as Dulbecco's modified eagle's medium (DMEM). Specifically, it may be carried out by diluting the sampled blood or biological fluid with a buffer solution, or adding the sampled blood or biological fluid to a liquid medium for dilution. The dilution process provides a protein concentration lower than that of the sampled blood or biological fluid.

Alternatively, after the agglutination of blood cells, the blood or biological fluid may be diluted and then subjected to centrifugation. The dilution may be performed as described above.

Moreover, from the standpoint of reducing the number of blood cells in advance to improve adhesion or adsorption of specific cells such as cancer cells and stem cells, the cell analysis method preferably includes bringing the blood or biological fluid into contact with a component having fibrinogen adsorbed thereto before the introduction (e.g., injection or dropwise addition) into the medical analysis device. For example, when the component having fibrinogen adsorbed thereto is a blood collection syringe, a blood collection tube, or a centrifuge tube, the above-mentioned advantageous effect can be significantly achieved.

EXAMPLES

The present invention is specifically described with reference to examples below, but is not limited thereto.

Example 1

A 0.25% by mass solution of "SIM6492.7" (Gelest Inc., 2-[methoxy(polyethyleneoxy)propyl]trimethoxysilane, $CH_3O-(CH_2CH_2O)_{6-9}-(CH_2)_3Si(OCH_3)_3$) in water/methanol (50% by mass/50% by mass) was prepared.

The solution in an amount of 100 µL was injected into a chamber slide (slide glass part: soda-lime glass, chamber size: 20 mm×20 mm) and allowed to stand at room temperature (17 hours), followed by drying in vacuum at 50° C. for six hours and then washing with water. Thus, an analysis device in which a hydrophilic silane compound layer was formed was prepared.

Example 2

An analysis device was prepared as in Example 1, except that the "SIM6492.7" (Gelest, Inc.) was changed to "SIM6492.72" (Gelest Inc., 2-[methoxy(polyethyleneoxy)-propyl]trimethoxysilane, $CH_3O-(CH_2CH_2O)_{9-12}-(CH_2)_3Si(OCH_3)_3$).

Example 3

An analysis device was prepared as in Example 1, except that the "SIM6492.7" (Gelest, Inc.) was changed to "SIM6492.73" (Gelest Inc., 2-[methoxy(polyethyleneoxy)-propyl]trimethoxysilane, $CH_3O—(CH_2CH_2O)_{21-24}$-$(CH_2)_3Si(OCH_3)_3$).

Example 4

An analysis device was prepared as in Example 1, except that the "SIM6492.7" (Gelest, Inc.) was changed to "SIM6493.4" (Gelest Inc., methoxytriethyleneoxypropyltrimethoxysilane, $CH_3O—(CH_2CH_2O)_3(CH_2)_3Si(OCH_3)_3$).

Example 5

An analysis device was prepared as in Example 1, except that the "SIM6492.7" (Gelest, Inc.) was changed to "SIM6493.7" (Gelest, Inc., methoxytriethyleneoxyundecyltrimethoxysilane, $CH_3O—(CH_2CH_2O)(CH_2)_{11}Si(OCH_3)_3$).

Example 6

A 0.25% by mass solution of "SIM6492.7" (Gelest Inc., 2-[methoxy(polyethyleneoxy)propyl]trimethoxysilane, $CH_3O—(CH_2CH_2O)_{6-9}$-$(CH_2)_3Si(OCH_3)_3$) in water/methanol (50% by mass/50% by mass) was prepared.

The solution in an amount of 100 μL was injected into a chamber slide (slide glass part: soda-lime glass, chamber size: 20 mm×20 mm) and allowed to stand at room temperature (17 hours), followed by drying in vacuum at 50° C. for six hours and then washing with water. Thus, a hydrophilic silane compound layer was formed.

Further, fibronectin was adsorbed onto the surface of the hydrophilic silane compound layer. Specifically, a 200 μg/mL solution of fibronectin in a PBS solution (phosphate buffered saline) was prepared and then left on the surface at 40° C. for one hour, followed by washing with a PBS solution to prepare an analysis device.

Comparative Example 1

An (untreated) chamber slide (slid glass part: soda-lime glass, chamber size: 20 mm×20 mm) was used.

The medical analysis devices prepared in the examples and comparative example were evaluated as described below. Table 1 shows the results.

[Thickness of Hydrophilic Silane Compound Layer (Coating Layer)]

The thickness of the hydrophilic silane compound layer on the inner surface of the well was measured (photographed) using a TEM at an accelerating voltage of 15 kV and a magnification of 1,000 times.

[Analysis of Whole Blood Spiked with Cancer Cells]

Stained human colon adenocarcinoma (HT-29) cells were suspended in whole blood at a concentration of 100 cells per mL of blood to prepare spiked blood. The spiked blood was diluted with an equal volume of a liquid medium to prepare a spiked blood dilution. Next, to a 15 ml centrifuge tube were added a separation liquid (LymphoPrep, density=1.077±0.001 g/mL) and then the spiked blood dilution, followed by centrifugation at 800 G for 20 minutes at room temperature (23° C.). Then, a mononuclear cell layer was separated. To the separated mononuclear cell layer was added a phosphate buffer (PBS) solution, followed by centrifugation again to enrich the mononuclear cell layer. After the centrifugation, the aggregates at the lowermost layer were suspended in a liquid medium containing 10% fetal bovine serum (FBS) in a volume equal to the initial whole blood volume. A 1 ml portion of the suspension was injected into the chamber slide and left at 37° C. for one hour to cause adhesion. Then, non-adhered cells were washed away with a PBS solution. Thereafter, the number of adhered cancer cells was counted using a fluorescence microscope. It should be noted that the numbers of adhered cancer cells are relative to that of Comparative Example 1 which is taken as 100.

TABLE 1

|  | Example | | | | | | Comparative Example |
| --- | --- | --- | --- | --- | --- | --- | --- |
|  | 1 | 2 | 3 | 4 | 5 | 6 | 1 |
| Thickness (nm) of hydrophilic silane compound layer | 4 | 5 | 9 | 2 | 12 | 14 | — |
| Number of adhered cancer cells in spiked blood analysis | 294 | 239 | 221 | 189 | 196 | 255 | 100 |

In Examples 1 to 6 in which a hydrophilic silane compound layer was formed, the number (relative value) of adhered cancer cells was greatly enhanced compared to Comparative Example 1 using a glass surface.

REFERENCE SIGNS LIST 1 multi-well plate
2 chamber slide
3 single well (dish)
11 well
21 hydrophilic silane compound layer
31 fibronectin

The invention claimed is:

1. A medical analysis device for capturing cancer cells or stem cells, comprising a well portion capable of containing a biological sample introduced therein, wherein
the well portion has an exposed hydrophilic silane compound layer formed at least partly on an inner surface of a bottom thereof,
the well portion is formed from at least one selected from the group consisting of a transparent resin, borosilicate glass, and soda-lime glass,
the hydrophilic silane compound layer has the ability to bind cancer cells or stem cells contained in a biological sample introduced into the well portion, and
the hydrophilic silane compound is a compound represented by the following formula (I):

$$R^{11}—O—(R^{12}O)_m—R^{13}—Si(X^{11})_n(X^{12})_{3-n} \quad (I)$$

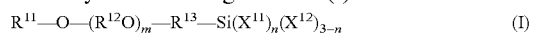

wherein $R^{11}$ represents a monovalent hydrocarbon group; $R^{12}$ and $R^{13}$ are the same or different and each represent a divalent hydrocarbon group;

each $X^{11}$ independently represents an alkoxy group;
each $X^{12}$ independently represents a monovalent hydrocarbon group or a halogen group;
m represents 1 to 50; and
n represents 0 to 3.

2. The medical analysis device according to claim 1, wherein the silane compound of formula (I) is a compound represented by the following formula (I-1):

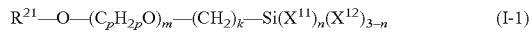  (I-1)

wherein $R^{21}$ represents a methyl group or an ethyl group;
each $X^{11}$ independently represents an alkoxy group;
each $X^{12}$ independently represents a monovalent hydrocarbon group or a halogen group;
p represents 1 to 8;
m represents 1 to 50;
n represents 0 to 3; and
k represents 1 to 20.

3. The medical analysis device according to claim 1, wherein the hydrophilic silane compound layer has fibronectin adsorbed thereto.

4. The medical analysis device according to claim 1, wherein the hydrophilic silane compound layer has a thickness of 1 to 30 nm.

5. The medical analysis device according to claim 3, wherein the hydrophilic silane compound layer has a thickness of 1 to 30 nm.

6. A cell analysis method for examining cells present in blood or biological fluid, wherein the method comprises:
providing the medical analysis device according to claim 1;
fractionating blood or biological fluid by centrifugation to collect specific cells from the blood or biological fluid;
capturing the specific cells from the collected liquid onto the hydrophilic silane compound layer using the medical analysis device; and
examining the specific cells.

7. The cell analysis method according to claim 6, wherein a separation liquid is used in the fractionation by centrifugation.

8. The cell analysis method according to claim 7, wherein the separation liquid has a density of 1.060 to 1.115 g/mL.

9. The cell analysis method according to claim 6, wherein the centrifugation is carried out using a container whose inner surface at least partly has a contact angle with water of 30 degrees or less.

* * * * *